US006304848B1

United States Patent
Singer

(12) United States Patent
(10) Patent No.: US 6,304,848 B1
(45) Date of Patent: Oct. 16, 2001

(54) MEDICAL RECORD FORMING AND STORING APPARATUS AND MEDICAL RECORD AND METHOD RELATED TO SAME

(75) Inventor: Michael A. Singer, Alachua, FL (US)

(73) Assignee: Medical Manager Corp., Alachua, FL (US)

( * ) Notice: Subject to any disclaimer, the term of this patent is extended or adjusted under 35 U.S.C. 154(b) by 0 days.

(21) Appl. No.: 09/133,548

(22) Filed: Aug. 13, 1998

(51) Int. Cl.$^7$ .............................. G06F 17/60; G10L 3/00

(52) U.S. Cl. ................... 705/3; 704/3; 704/215; 704/240; 704/251; 704/254; 704/255; 704/270

(58) Field of Search ................ 705/3, 2; 704/3, 704/215, 240, 251, 254, 255, 270

(56) References Cited

U.S. PATENT DOCUMENTS

| 3,697,693 | 10/1972 | Dechenes et al. ............. 340/149 |
|---|---|---|
| 4,130,881 | 12/1978 | Haessler et al. ............. 364/900 |

(List continued on next page.)

FOREIGN PATENT DOCUMENTS

0862159A1 * 2/1998 (EP) ........................ G10L/3/00

OTHER PUBLICATIONS

IBM:IBM launches ViaVoice Gold Healthcare Vocabulary at Healthcare '98, Harrogate, Ms Presswire, Mar. 1998.*

Voice Recognition for Physicians, vol. III: http://www.hawaiian.net/alohaweb/speechrecognition/physicians.htm, Jun. 1997.*

(List continued on next page.)

*Primary Examiner*—Eric W. Stamber
*Assistant Examiner*—Yehdega Retta
(74) *Attorney, Agent, or Firm*—Allen, Dyer, Doppelt, Milbrath & Gilchrist, P.A.

(57) ABSTRACT

An apparatus and method for forming medical records and a medical record formed thereby are provided. The apparatus preferably includes a voice input device for inputting free dictation of medical personnel, a voice processor responsive to the voice input device for processing the inputted voice and generating voice data therefrom, and a key term recognizer responsive to the voice processor for recognizing key medical terms freely dictated by the medical personnel. The key term recognizer preferably includes a key medical term database for storing a plurality of key medical terms therein. The apparatus preferably also includes a medical term matcher responsive to the key word recognizer for matching recognized key medical terms used by the medical personnel at least with patient conditions to thereby add additional data thereto and a medical record creator responsive to the medical term matcher for creating an actual patient medical record therefrom. A method of forming medical records preferably includes generating a plurality of key medical terms, recognizing the plurality of key medical terms responsive to a key medical term database having a plurality of key medical terms stored therein, matching recognized key medical terms used by the medical personnel at least with known patient conditions stored in a knowledge database so that the knowledge database assists in further describing the actual condition of the patient by adding additional data thereto, and creating an actual patient medical record responsive to the matched recognized key medical terms.

55 Claims, 4 Drawing Sheets

U.S. PATENT DOCUMENTS

| | | | | |
|---|---|---|---|---|
| 4,290,114 | | 9/1981 | Sinay | 364/900 |
| 4,491,725 | | 1/1985 | Pritchard | 235/375 |
| 4,648,037 | | 3/1987 | Valentino | 364/408 |
| 4,730,259 | | 3/1988 | Gallant | 364/513 |
| 4,733,354 | | 3/1988 | Potter et al. | 364/415 |
| 4,839,822 | | 6/1989 | Dormond et al. | 364/513 |
| 4,858,121 | | 8/1989 | Barber et al. | 364/406 |
| 4,866,778 | | 9/1989 | Baker | 364/513 |
| 4,872,122 | | 10/1989 | Altschuler et al. | 364/554 |
| 4,907,191 | | 3/1990 | Sato | 364/900 |
| 4,916,611 | | 4/1990 | Doyle, Jr. et al. | 364/401 |
| 5,005,143 | | 4/1991 | Altschuler et al. | 364/554 |
| 5,018,067 | | 5/1991 | Mohlenbrock et al. | 364/413 |
| 5,027,406 | | 6/1991 | Roberts et al. | 381/43 |
| 5,146,439 | * | 9/1992 | Jachmann et al. | 369/25 |
| 5,197,052 | | 3/1993 | Schroder et al. | 369/25 |
| 5,231,670 | | 7/1993 | Goldhor et al. | 381/43 |
| 5,265,075 | | 11/1993 | Bergeron et al. | 369/25 |
| 5,274,738 | | 12/1993 | Daly et al. | |
| 5,305,205 | * | 4/1994 | Weber et al. | 364/419 |
| 5,327,341 | | 7/1994 | Whalen et al. | 364/413 |
| 5,428,707 | | 6/1995 | Gould et al. | |
| 5,517,405 | | 5/1996 | McAndrew et al. | 364/413 |
| 5,544,654 | | 8/1996 | Murphy | 128/660 |
| 5,660,176 | * | 8/1997 | Iliff | 600/300 |
| 5,671,426 | | 9/1997 | Armstrong, III | 395/760 |
| 5,692,220 | | 11/1997 | Diamond et al. | 395/924 |
| 5,823,948 | * | 10/1998 | Ross, Jr. et al. | 705/3 |
| 5,867,821 | * | 2/1999 | Ballantyne et al. | 705/2 |
| 6,031,526 | * | 2/2000 | Shipp | 345/302 |
| 6,092,044 | * | 7/2000 | Baker et al. | 704/254 |

OTHER PUBLICATIONS

Voice Recognition for Physicians; http://www.hawaiian.net/alohaweb/speechrecognition/article–397.htm, Mar. 1998.*

Dragon: New medical speech dictation software from dragon offers major savings in the transcription costs; M2 Presswire; Coventry; http://proquest.umi.com/pqdweb?TS=93870 . . . &Fmt=3&IDx=1 &RQT=309&Dtp=1, Apr. 22, 1998.*

The Kurzweil Applied Intelligence Alumni Newsletter; Listen to Me; http://airtight.com/kan/kcrpc.htm., Oct. 1996.*

L&H Clinical Reporter—Structred Data Reporting –L&H; http://www.lhsl.com/clinicalreporter/structure.as, Oct. 1996.*

* cited by examiner

MEDICAL RECORD FORMING AND STORING APPARATUS AND MEDICAL RECORD AND METHOD RELATED TO SAME

FIELD OF THE INVENTION

This invention is related to the medical office automation industry and more particularly to the field of forming medical records in the medical industry.

BACKGROUND OF THE INVENTION

Over the years, various office automation equipment has been developed for providing offices with automatic systems for dictation, transcription, word processing, financial analysis, and other office functions which could be automated. This office automation equipment generally applied to all types of offices including sales, financial, legal, insurance, research, medical and various service or other business offices. Each type of office or general field of the office, however, often has their own constraints and problems for office automation equipment. The medical field, for example, has attempted to automate the diagnosis of a patient's illness based upon a patient's symptoms and then often recommended a corresponding patient treatment. Examples of such systems can be seen in U.S. Pat. No, 4,733,354 by Potter et al. titled "Method And Apparatus For Automated Medical Diagnosis Using Decision Tree Analysis," U.S. Pat. No. 4,839,822 by Dormond et al. titled "Computer System And Method For Suggesting Treatments For Physical Trauma," U.S. Pat. Nos. 4,872,122 and 5,005, 143 by Atlschuler et al. and each titled "Interactive Statistical System And Method For Predicting Expert Decisions," and U.S. Pat. No. 5,692,220 by Diamond et al. "Decision Support System And Method For Diagnosis Consultation In Laboratory Hematopathology." Although such systems can have a role in medical office and hospital automation, such systems are often limited to a research location, e.g., using a knowledge base which correlates patient symptoms to diagnosis of an illness and/or recommendations of a treatment, for only selective uses. In other words, the physician or other medical personnel remain the primary patient contact and interface, and diagnosis and treatment decisions usually remain substantially in the hands of the physician.

Because the physician or other medical personnel, e.g., nurses, nurse assistants, technicians, remain the primary patient contact and primary decision maker, the physician or other medical personnel are also primarily responsible for creating the medical record or history of a patient such as the creating or forming of a progress note or narrative description during a patient encounter. These medical records often become more and more critical to an office, hospital, or other organization, e.g., the medical records representing a complete record of a patient's health care administered by a physician, other medical personnel, or the facility in general. Accordingly, attempts have been made over the years to automate the medical history taking process. Examples of such attempts can be seen in U.S. Pat. No. 4,130,881 by Haessler et al. titled "System And Technique For Automated Medical History Taking," U.S. Pat. No. 5,146,439 by Jachmann et al. titled "Records Management System Having Dictation/Transcription Capability," U.S. Pat. No. 5,265,075 by Bergeron et al. titled "Voice Processing System With Editable Voice Files," and U.S. Pat. No. 5,327,341 by Whalen titled "Computerized File Maintenance System For Managing Medical Records Including Narrative Reports."

Some of these automated medical record forming systems, for example, require that a user enter information about a patient into selected fields so that the medical record is formed by question and answer prompts or data entry into what is essentially a form, e.g., based upon a limited set of predetermined answers to a prompted question. Others of these systems merely allow transcribed files to be accessed again or allow portions of files which are similar to not need repetition. Such systems, however, provide little utility for a physician directly and require that the physician adapt to some style, format, language usage, or other constraints of the automated system and provide little or no freedom for the physician's own style. Additionally, such systems often require additional personnel to transcribe, enter and manage the forms and require personnel training and learning of the particular format used by the system. Others of these automated medical record forming and management systems often record and transcribe dictation for entry into a computer or database which then can create, update, and manage medical records. Some of these systems allow a physician to dictate but require a transcriber to extract pertinent sections from the dictated report for entry into the computer in predefined categories. Accordingly, these systems also require additional personnel to transcribe dictation, enter and manage the forms, and to be trained and learn the particular format used by the system.

SUMMARY OF THE INVENTION

In view of the foregoing, the present invention advantageously provides an apparatus and method for forming a medical record which does not require a separate transcriptionist for transcribing a dictated medical record. The present invention also advantageously provides an apparatus and method for forming a medical record which allows a physician or other medical personnel to freely dictate medical data related to a medical record so that the resulting product will be a medical record in either a selected or predetermined format. The present invention additionally advantageously provides an apparatus and method for forming a medical record which recognizes free, unprompted, and unstructured speech from a physician or other medical personnel and responsively translates the speech into a structured medical record format which is either selected by the user or predetermined by the user or system. The present invention also additionally provides an apparatus and method for forming a medical record which recognizes key medical words or terms in the free, unprompted, and unstructured dictation so that relationships can be made between the medical terms, other related medical terms, a patient's conditions, and potential treatments to thereby form at least a draft medical record therefrom. The present invention further advantageously provides a medical record which is structured or formed from a relationship between medical terms used by a physician or other medical personnel and other related medical terms, patient conditions, and potential treatments. The present invention still further advantageously provides a medical record which is formed by free, unprompted, and unstructured dictation by a physician or other medical personnel by recognizing key medical words or terms in the dictation to thereby form a medical record based upon either a selected or predetermined format.

More particularly, a medical record forming and storing apparatus is provided which preferably includes voice inputting means, e.g., preferably provided by a voice recorder, for inputting the unprompted and unstructured free dictation of at least one medical personnel such as a physician, voice processing means, e.g., preferably provided by a voice processor, responsive to the voice inputting means for processing the recorded voice from the voice inputting means and generating voice data therefrom, and key term recognizing means, e.g., preferably provided by a key term recognizer, responsive to the voice processing means for recognizing key medical terms freely dictated by the at least one medical personnel. The apparatus also preferably includes medical term matching means, e.g., preferably provided by a medical term matcher, responsive to the key term recognizing means for matching medical terms used by the at least one medical personnel at least with patient conditions and/or treatments. The medical term matching means preferably includes a knowledge database relating patient conditions with patient treatments of the conditions so that the knowledge base assists in further describing at least the actual condition and/or treatment of the patient by adding additional data, e.g., a more complete description, to a medical form which is or will be created. The apparatus can further include medical record creating means, e.g., preferably provided by a medical record creator, responsive to the medical term matching means for creating an actual patient medical record therefrom.

As used herein, the term free dictation means the unstructured and unprompted dictation of the at least one medical personnel, e.g., a physician. By unstructured and unprompted, it is recognized that words, sentences, and paragraphs have structure which often prompts additional structure such as a limited set of predetermined answers to a prompted question. Nevertheless, this is not the intent of the meaning of unstructured and unprompted. Rather, medical personnel such as physicians are allowed to freely dictate words, terms, sentences, phrases, paragraphs, and other language structure without the necessity of using only selected words, terms, phrases, paragraphs, and other structure required by the system into which the physician or other medical personnel dictates or speaks. In other words, the dictation does not have to be within a given format required by the medical record forming system outside of normal language usage by the speaking or speech of the medical personnel and is preferably not based upon a limited set of predetermined answers to a prompted question.

By advantageously using or keying off of key medical terms used by a physician or other medical personnel such as in free, unprompted, and unstructured dictation, the apparatus and method provide freedom for the physician to talk, speak, and dictate according to the physician's personal preferences, style, language, vocabulary, tone, and other desires when forming a medical record. Non-key medical terms or other unrecognized words, for example, can advantageously be discarded or stored for future reference. The physician, for example, does not have to fit within the constraints or format requirements of the system which receives the dictation and forms the medical record therefrom. Because the free dictation is the preferred format and key medical terms are recognized by the apparatus, additional personnel to transcribe the physician's dictation are not needed.

According to one aspect of the present invention, the key term recognizing means, for example, can include key medical term storing means for storing a plurality of key medical terms, comparing means responsive to the key medical term storing means for comparing the voice data with key medical terms within the key medical term storing means, and separating means responsive to the comparing means for separating the key medical terms from the non-key medical terms.

According to another aspect of the present invention, the medical record creating means, for example, can advantageously include draft record generating means for generating a draft medical record related to the at least one medical personnel's dictation for review by the at least one medical personnel, record revising means responsive to the at least one medical personnel for revising the draft medical record, and record accepting means responsive to the at least one medical personnel for accepting the draft medical record.

According to still further aspects of the present invention a medical recording forming and storing apparatus preferably includes a voice input device for inputting dictation of at least one medical personnel, a voice processor responsive to the voice input device for processing the inputted voice and generating voice data therefrom, a key term recognizer responsive to the voice processor for recognizing key medical terms dictated by the at least one medical personnel. The key term recognizer preferably includes a key medical term database for storing a plurality of key medical terms therein. The apparatus also preferably includes a medical term matcher responsive to the key word recognizer for matching recognized key medical terms used by the at least one medical personnel with patient conditions and/or treatments to thereby add additional data thereto.

The present invention also advantageously provides a medical record having a selected format. The medical record preferably includes a plurality of primary key medical terms responsively generated by the voice of at least one medical personnel and arranged in the selected format. The primary key medical terms are preferably generated by the free, unprompted, and unstructured dictation of the at least one medical personnel and preferably include at least patient conditions and treatments. The medical record also includes additional secondary text responsively generated by the presence of the primary key medical terms and arranged in the selected format. The additional secondary text preferably at least includes medical terms describing patient conditions and/or treatments related to the plurality of primary key medical terms describing patient conditions and/or treatments but not being a subset of the plurality of primary key medical terms.

The present invention yet further provides methods of forming a medical record. A method of forming medical records preferably includes generating a plurality of key medical terms, recognizing the plurality of key medical terms responsive to a key medical term database having a plurality of key medical terms stored therein, matching recognized key medical terms used by the at least one medical personnel with known patient conditions and treatments stored in a knowledge database which relates patient conditions with patient treatments of the conditions so that the knowledge base assists in further describing at least the actual condition and/or treatment of the patient by adding additional data thereto, and creating an actual patient medical record responsive to the matched recognized key medical terms.

Another method of forming medical records according to the present invention preferably includes inputting unprompted and unstructured free dictation of at least one medical personnel, processing the inputted voice to thereby generate voice data therefrom, recognizing key medical terms freely dictated by the at least one medical personnel responsive to a key medical term database having a plurality of key medical terms stored therein, matching recognized key medical terms used by the at least one medical personnel with known patient conditions and/or treatments to thereby add additional data thereto, and creating an actual patient medical record therefrom.

Yet another method of forming medical records according to the present invention preferably includes inputting dictation of at least one medical personnel, processing the recorded voice to thereby generate voice data therefrom, recognizing key medical terms dictated by the at least one medical personnel responsive to a key medical term database having a plurality of key medical terms stored therein, and matching recognized key medical terms used by the at least one medical personnel with known patient conditions and/or treatments to thereby add additional data thereto.

By providing a knowledge database, or other knowledge storage medium which at least includes patient conditions and/or also preferably patient treatments or potential treatments related to a corresponding patient condition, the present invention advantageously provides an apparatus and method of forming a medical record which adds additional text which are also preferably related to the same patient conditions and/or treatments to the existing medical terms to provide a more complete record or a record according to either a selected or predetermined format to thereby further describe additional data or information desired to be in a medical record. This feature, for example, can advantageously allow a physician or other medical personnel to dictate as desired and yet have some assurance that the first draft of the medical record will be fairly complete. The physician, for example, can then revise the medical record. By reference to the same knowledge database for checking on the impact of the revised or additional terms provided by the physician with the terms added from the knowledge database, the apparatus can then provide a revised medical record. Such revisions advantageously can be repeated until the medical record is acceptable to the physician.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF PREFERRED EMBODIMENTS

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime and double prime notation, if used, indicate similar elements in alternative embodiments.

Figure 1:
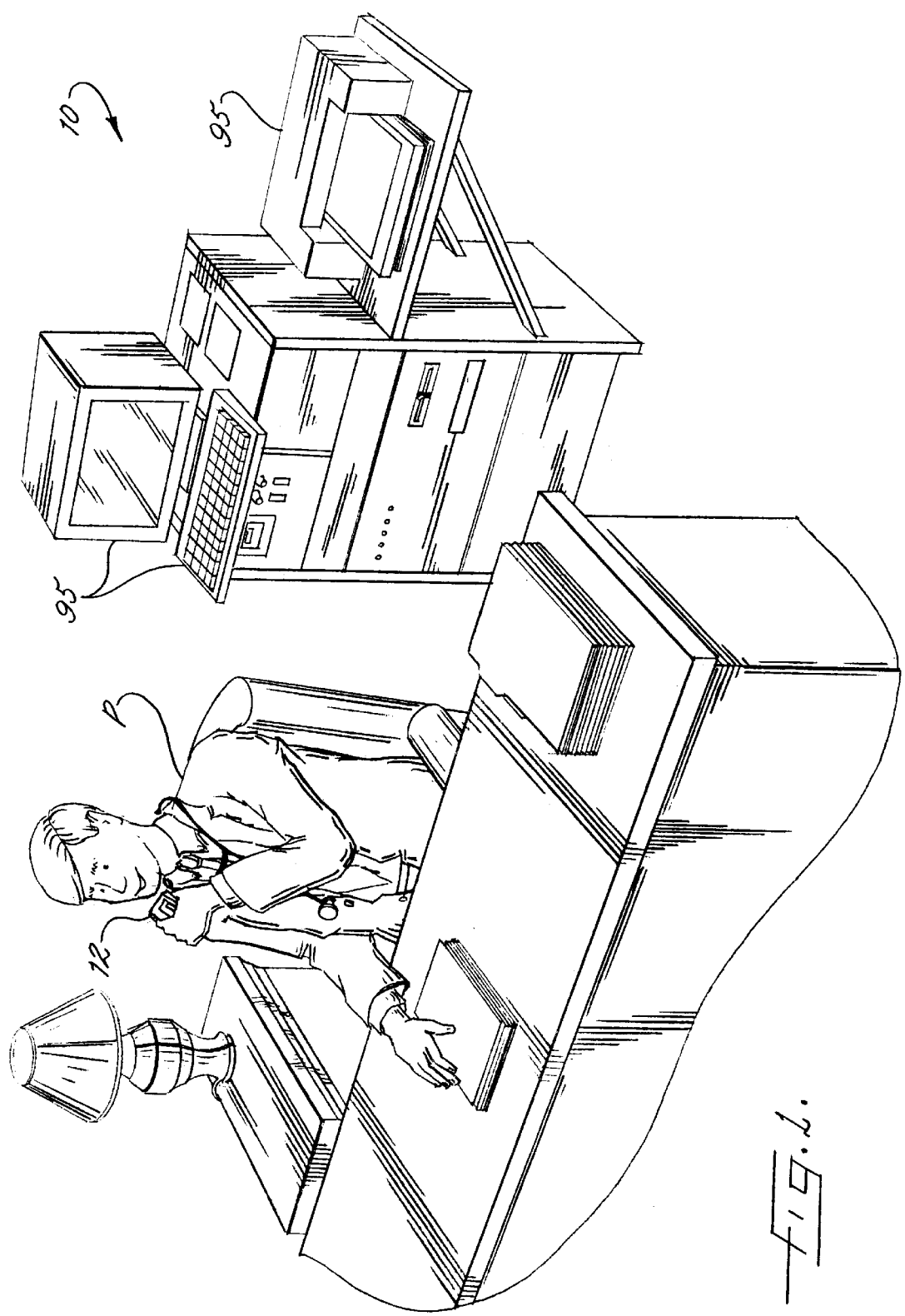
FIG. 1 is an environmental view of a physician freely dictating to a medical record forming and storing apparatus according to the present invention.
Figure 2:
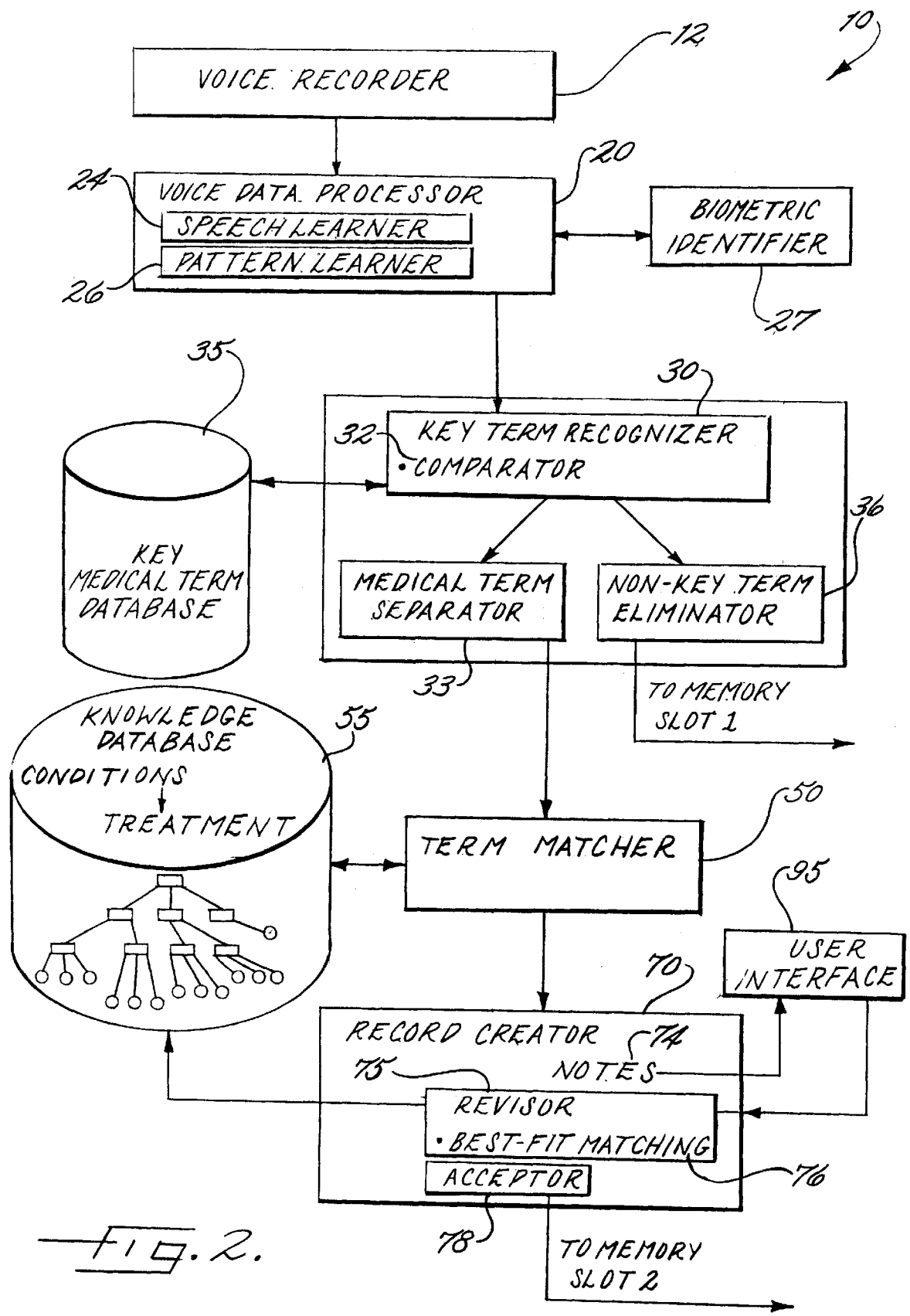
FIG. 2 is a block diagram of a medical record forming and storing apparatus according to the present invention.

FIGS. 1–2 illustrate an apparatus 10 for forming and storing medical records 15 (see, e.g., FIG. 4) according to the present invention which preferably uses a combination of hardware elements and software programs and/or databases for forming the apparatus. The medical record forming and storing apparatus 10 preferably includes voice inputting means, e.g., preferably provided by a voice recorder 12, for inputting the unprompted and unstructured free dictation of at least one medical personnel such as a physician, and voice processing means, e.g., preferably provided by a voice processor or voice data processor 20 such as one or more microprocessors, microcontrollers, digital processing devices or circuits, software processors, computer voice recognition software, or other data processors as understood by those skilled in the art, responsive to the voice inputting means 12 for processing the freely dictated voice from the voice inputting means 12 and generating voice data therefrom. As understood by those skilled in the art, the voice recorder 12, for example, can be any of various types of audio tape, digital media recorders, direct dictation into a software program, or other voice input devices such as produced by companies such as Dictaphone, Lanier, Pitney Bowes, IBM, Microsoft, Dragon Systems, or Kurzweil Applied Intelligence. The voice processor 20 preferably includes at least one microprocessor having stored commands for processing data and/or other hardware and software as understood by those skilled in the art.

As set forth herein, the term free dictation means the unstructured and unprompted dictation of the at least one medical personnel. By unstructured and unprompted, it is recognized that words, sentences, and paragraphs have structure which often prompts additional structure such as a limited set of predetermined answers to a prompted question. Nevertheless, this is not the intent of the meaning of unstructured and unprompted. Rather, medical personnel such as physicians are allowed to dictate words, terms, sentences, phrases, paragraphs, and other language structure without the necessity of using only selected words, terms, phrases, paragraphs, and other structure required by the system or apparatus 10 into which the physician or other medical personnel dictates or speaks. In other words, the dictation does not have to be within a given format required by the medical recording forming system or apparatus 10 outside of normal language usage by the speaking of the medical personnel and is preferably not based upon a limited set of predetermined answers to a prompted question.

By advantageously using or keying off of key medical terms used by a physician P or other medical personnel such as in free, unprompted, and unstructured dictation, the apparatus 10 and method of the present invention provide freedom to the physician P to talk, speak, and dictate according to the physician's personal preferences, style, language, vocabulary, tone, and other desires when forming a medical record. Non-key medical terms or other unrecognized words, for example, can advantageously be discarded or stored for future reference. The physician P, for example, does not have to fit within the constraints or format requirements of the system or apparatus 10 which receives the dictation and forms the medical record therefrom. Because the free dictation is the preferred format and key medical terms are recognized by the apparatus 10, additional personnel to transcribe the physician's dictation are not needed.

The voice processing means 20 also can advantageously include speech term learning means, e.g., a speech learner 24 such as formed in software and/or hardware as understood by those skilled in the art, for learning speech terms used by identified medical personnel and/or speech pattern learning means, e. g., a pattern learner 26 such as formed in software and/or hardware as understood by those skilled in the art, for learning speech patterns used by identified medical personnel. To perform these functions, for example, the apparatus 10 can also include biometric identifying means 27 connected to the voice processing means 20 for identifying biometric data from medical personnel to thereby reference previous terms or patterns from previous dictations to the apparatus by the identified medical personnel. As understood by those skilled in the art, the biometric identifying means is preferably a voice identification pattern, tone, or other voice identifier 27. Other biometric identifiers, however, such as fingerprint characteristics, eye characteristics, skin characteristics, body fluid characteristics, or other user characteristics can be used as well according to the present invention.

The apparatus 10 preferably also has key term recognizing means, e.g., preferably provided by a key term recognizer 30, responsive to the voice processor 20 for recognizing key medical terms freely dictated by the at least one medical personnel. The key term recognizing means 30, for example, can include key medical term storing means, such as a key medical term database 35, for storing a plurality of key medical terms, comparing means, e.g., a comparator 32, responsive to the key medical term storing means for comparing the voice data with key medical terms within the key medical term storing means, and separating means, e.g., a medical term separator 33 such as provided by a natural language parser as understood by those skilled in the art, responsive to the comparing means for separating the key medical terms from the non-key medical terms. The key term recognizing means 30 can also advantageously include non-key term eliminating means, e.g., a non-key term eliminator 36, for eliminating non-key terms from the generated voice data. The key term recognizing means 30 can additionally include non-key term storing means, e.g., a memory slot 1, responsive to the non-key term eliminating means 36 for storing the eliminated non-key terms for future reference.

The apparatus 10 also preferably includes medical term matching means, e.g., preferably provided by a medical term matcher formed in software or a predetermined stored commands, responsive to the key term recognizing means 30 for matching medical terms used by the at least one medical personnel at least with patient conditions, and also with treatments as well. The medical term matching means 50 preferably includes a knowledge database 55 relating patient conditions with additional condition data, words, terms, and, if desired, even patient treatments of the conditions so that the knowledge base assists in further describing at least the actual condition and/or treatment of the patient by adding additional data to a medical record 15 which is or will be created. The matching preferably includes a comparator software subroutine or other matching routine as understood by those skilled in the art. The comparator preferably systematically compares the medical term with other data or terms related thereto or exactly matching in a database.

By providing a knowledge database 55, or other knowledge storage medium which at least includes patient conditions and/or also preferably patient treatments or potential treatments related to a corresponding patient condition, the apparatus 10 advantageously can add additional medical terms also preferably related to the same patient conditions and/or treatments to the existing medical terms to more completely describe at least the patient condition and thereby provide a more complete record or a record 15 according to either a selected or predetermined format to thereby further describe additional data or information desired to be in a is medical record 15. As understood by those skilled in the art, the knowledge database 55 preferably has a structured tree configuration which enables each recognized key medical term, as well as sets or combinations of recognized key medical terms, to be searched for related medical terms such as patient conditions, diagnosis, and/or treatments. Such structural tree configurations are well known in the art and include nodes, branches, and leafs related to a root node such as illustrated in FIG. 2, which can relate the primary key medical terms dictated by the physician P to other secondary terms or text which should be included with the medical record which also relate to patient conditions, treatments, symptoms, or other desired data to also be added to the medical record 15 (see also FIG. 4).

This feature, for example, can advantageously allow a physician P or other medical personnel to dictate as desired and yet have some assurance that the first draft of the medical record 15 will be fairly complete. The physician P, for example, can then revise the medical record 15. By reference to the same knowledge database 55 for checking on the impact of the revised or additional terms provided by the physician P with the terms added from the knowledge database 55, the apparatus can then provide a revised medical record 15. Such revisions can be repeated until the medical record 15 is acceptable to the physician P.

Accordingly, the apparatus 10 can further include medical record creating means, e.g., preferably provided by a medical record creator 70, responsive to the medical term matching means 50 for creating an actual patient medical record 15 therefrom and medical record storing means, e.g., a memory slot 2, responsive to the medical record creating means 70 for storing an accepted medical record 15 created therefrom for future reference. The medical record creating means 70, for example, can advantageously include draft record generating means, e.g., illustrated by the notes 74 for generating a draft medical record related to the at least one medical personnel's dictation for review by the at least one medical personnel, record revising means, e. g., a revisor 75, responsive to the at least one medical personnel for revising the draft medical record, and record accepting means, e. g., an acceptor 78, responsive to the at least one medical personnel for accepting the draft medical record 15. The apparatus 10 can also include a medical personnel user interface 95 responsive to the medical record creating means for providing a user interface to medical personnel so that draft medical records can readily be revised. The user interface 95 is preferably provided by a display terminal, keyboard, mouse, and/or a printer for providing a means for revising the draft record or notes 15 (see FIGS. 1 and 4). The record revising means 75 preferably includes knowledge database revised term matching means, e. g., preferably provided by a best-fit matching software program 76 as understood by those skilled in the art, responsive to the knowledge database 55 for matching terms revised by the at least one medical personnel from the user interface 95 with terms in the knowledge database 55. The knowledge database revised term matching means 76 includes best-fit comparing means for comparing the revised term with terms within the knowledge database 55 based upon a best-fit matching configuration.

Figure 4:
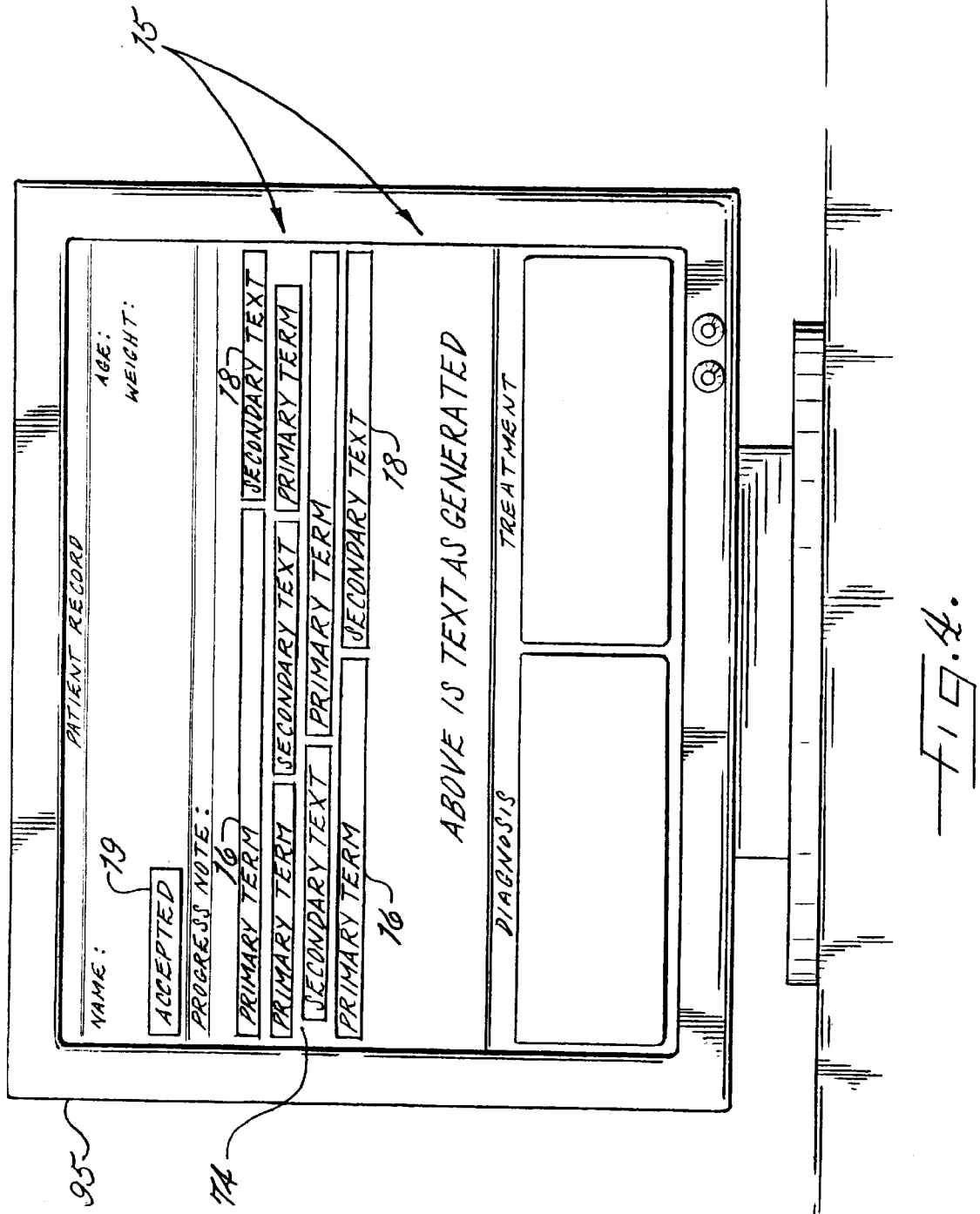
FIG. 4 is a schematic view of a medical record such as created or formed from a patient encounter and having primary key medical terms and secondary text according to the present invention.

As perhaps best illustrated in FIG. 4, the present invention also advantageously provides a medical record 15 having a selected format such as produced from a patient encounter by a physician or other medical personnel. The medical record 15 preferably is a progress note or narrative description of a patient encounter and preferably includes a plurality of primary key medical terms 16 responsively generated by the voice of at least one medical personnel and arranged in the selected format. The primary key medical terms 16 are preferably generated by the free, unprompted, and unstructured dictation of the at least one medical personal and preferably include at least patient conditions and treatments. The medical record 15 also includes additional secondary text 18 responsively generated by the presence of the primary key medical terms 16, positioned interspersed with and adjacent each of the plurality of primary key medical terms, and arranged in the selected format. The additional secondary text 18 preferably is readable data, words, or other information and can include medical terms describing patient conditions and/or treatments related to the plurality of primary key medical terms 16 describing patient conditions and treatments but not being a subset of the plurality of primary key medical terms 16. The medical record 15 also can advantageously include at least one acceptance identifier 19 associated therewith for identifying that the medical record has been accepted by the at least one medical personnel whose voice generated the plurality of primary medical terms 16.

As illustrated in FIGS. 1–4, the present invention yet further provides methods of forming a medical record 15. A method of forming medical records 15 preferably includes generating a plurality of key medical terms 16, recognizing the plurality of key medical terms 16 responsive to a key medical term database 35 having a plurality of key medical terms stored therein, matching recognized key medical terms used by the at least one medical personnel with known patient conditions and treatments stored in a knowledge database 55 which relates patient conditions with patient treatments of the conditions so that the knowledge base 55 assists in further describing at least the actual condition and/or treatment of the patient by adding additional data thereto, e.g., more completely describing at least a condition and/or treatment, and creating an actual patient medical record responsive to the matched recognized key medical terms.

This method can also advantageously include storing a created medical record 15 accepted by at least one medical personnel for future reference. The recognizing step preferably includes eliminating non-key terms from generated data and storing the eliminated non-key terms for future reference. The creating step preferably includes generating a draft medical record related to the at least one medical personnel's dictation for review by the at least one medical personnel, revising the draft medical record responsive to the at least one medical personnel, and accepting the draft medical record. The revising step preferably includes providing a knowledge database revised term matcher 76 responsive to the knowledge database 55 for matching terms revised by the at least one medical personnel with terms in the knowledge database 55. The knowledge database revised term matcher 76 can advantageously include a best-fit comparator for comparing the revised term with terms within the knowledge database based upon a best-fit matching configuration. A user interface 95 to medical personnel can also be provided so that the draft medical records 15 can readily be revised.

Figure 3:
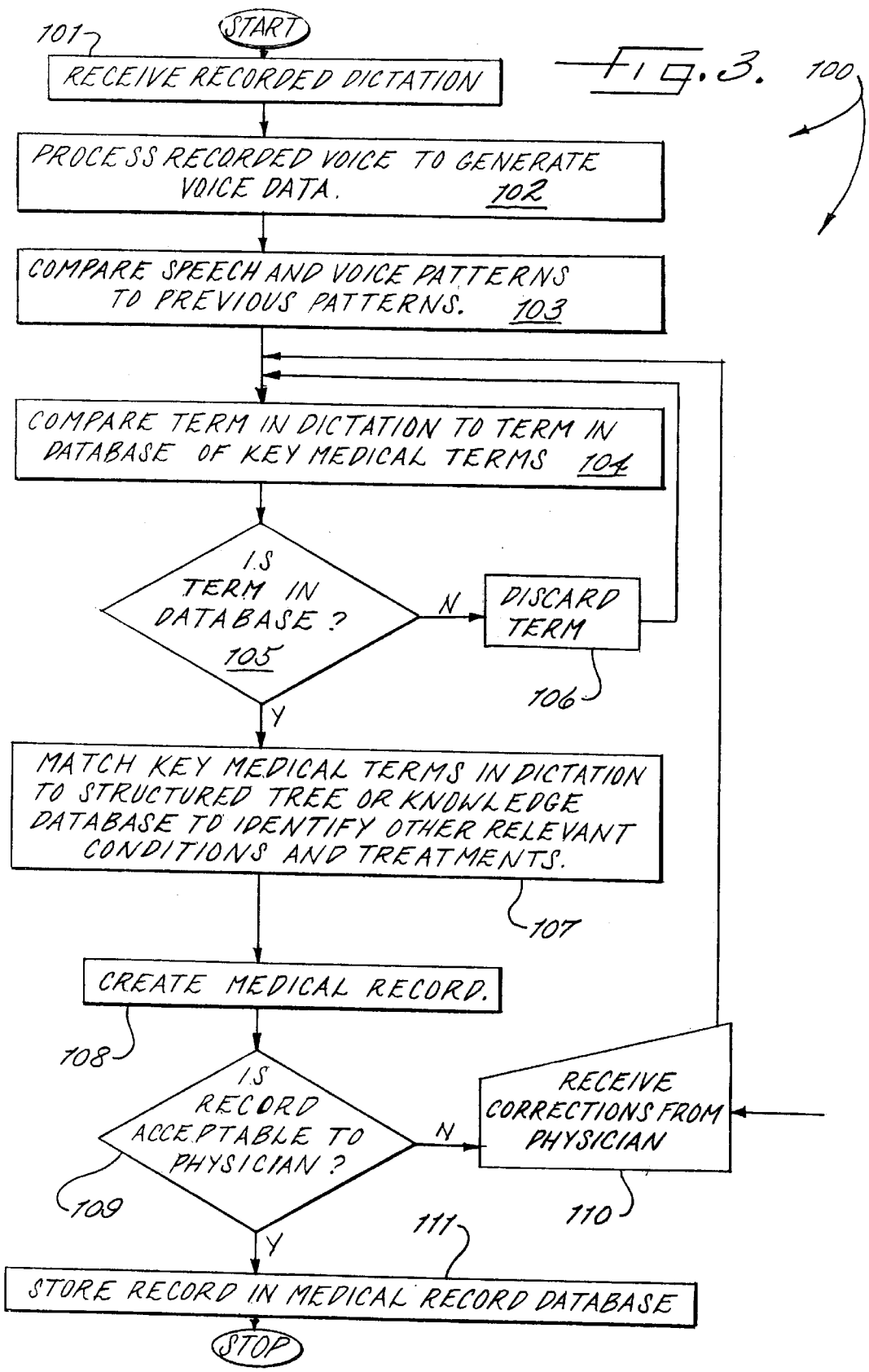
FIG. 3 is a block diagram of the operations of a medical record forming and storing apparatus according to the present invention.

Another method of forming medical records 15 according to the present invention, as perhaps best illustrated by the operational process 100 in FIG. 3, preferably includes inputting, e.g., receive and/or record, unprompted and unstructured free dictation of at least one medical personnel (Block 101), processing the inputted voice to thereby generate voice data therefrom (Block 102), recognizing key medical terms 16 freely dictated by the at least one medical personnel responsive to a key medical term database 35 having a plurality of key medical terms stored therein (Blocks 104–106), matching recognized key medical terms 16 used by the at least one medical personnel with known patient conditions and treatments to thereby add additional data thereto (Block 107), and creating an actual patient medical record 15 therefrom (Blocks 108–110).

The method can further include storing a created actual medical record 15 accepted by the at least one medical personnel for future reference (Block 111). The matching step preferably includes providing a knowledge database 55 having a structured tree configuration which relates patient conditions with patient treatments of the conditions so that the knowledge base 55 assists in further describing the actual condition of the patient by adding additional data thereto (Block 107). Also, the processing step can include learning speech terms used by identified medical personnel and/or learning speech patterns used by identified medical personnel (Block 103). The method can further include identifying biometric data from medical personnel to thereby reference previous terms or patterns from previous dictations by the identified medical personnel.

Further still, the recognizing step preferably includes eliminating non-key terms from the generated voice data (Block 106) and storing the eliminated non-key terms for future reference. The creating step can include generating a draft medical record related to the at least one medical personnel's dictation for review by the at least one medical personnel (Block 109), revising the draft medical record 15 responsive to the at least one medical personnel (Block 110), e.g., by further dictation such as indicated by the solid arrowed line above Block 104, by typing, using one or more fonts, softkeys, icons, or clicking on or selecting word, symbol, or phrase choices displayed on a display or screen and/or audibly heard as indicated by the broken arrowed lines above Blocks 107 and 108, and accepting the draft medical record (Block 109). The revising step preferably includes providing a knowledge database revised term matcher 76 responsive to the knowledge database 55 for matching terms revised by the at least one medical personnel with terms in the knowledge database 15. The knowledge database revised term matcher 76 preferably includes a best-fit comparator for comparing the revised term with terms within the knowledge 55 database based upon a best-fit matching configuration. A user interface to medical personnel is also preferably provided so that the draft medical records 15 can be revised therefrom.

Yet another method of forming medical records 15 according to the present invention preferably includes receiving dictation of at least one medical personnel, processing the received voice to thereby generate voice data therefrom, recognizing key medical terms dictated by the at least one medical personnel responsive to a key medical term database 35 having a plurality of key medical terms 16 stored therein, and matching recognized key medical terms used by the at least one medical personnel with known patient conditions and treatments to thereby add additional data, such as additional medical terms thereto.

This method can also include creating an actual patient medical record 15 responsive to the matched recognized key medical terms and storing a created medical record 15 accepted by the at least one medical personnel for future reference. The matching step can preferably include providing a knowledge database 55 having a structured tree configuration which relates patient conditions with patient treatments of the conditions so that the knowledge database 55 assists in further describing the actual condition of the patient by adding additional data thereto. Also, the processing step can include learning speech terms used by identified medical personnel and/or learning speech patterns used by identified medical personnel.

The method can further include identifying biometric data from medical personnel to thereby reference previous terms or patterns from previous dictations by the identified medical personnel. The recognizing step preferably includes eliminating non-key terms from the generated voice data and storing the eliminated non-key terms for future reference. The creating step can include generating a draft medical record 15 related to the at least one medical personnel's dictation for review by the at least one medical personnel, revising the draft medical record 15 responsive to the at least one medical personnel, and accepting the draft medical record 15. The revising step preferably includes providing a knowledge database revised term matcher 75 responsive to the knowledge database 55 for matching terms revised by the at least one medical personnel with terms in the knowledge database 55. The knowledge database revised term matcher 76 preferably includes a best-fit comparator for comparing the revised term with terms within the knowledge database 55 based upon a best-fit matching configuration. A user interface 95 to medical personnel is also preferably provided so that the draft medical records 15 can be revised therefrom.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A medical record forming and storing apparatus comprising:
   voice inputting means for inputting unprompted and unstructured free dictation of at least one medical personnel;
   voice processing means responsive to said voice inputting means for processing the inputted voice from said voice inputting means and generating voice data therefrom;
   key term recognizing means responsive to said voice data processing means for recognizing key medical terms freely dictated in an unstructured and unprompted format by the at least one medical personnel, said key term recognizing means including key medical term storing means for storing a plurality of key medical terms, comparing means responsive to said key medical term storing means for comparing the voice data with key medical terms within said key medical term storing means, separating means responsive to said comparing means for separating the key medical terms from the non-key medical terms, and non-key term eliminating means for eliminating non-key terms from the generated voice data;
   medical term matching means responsive to said key term recognizing means for matching medical terms used by the medical personnel at least with patient conditions, said medical term matching means including a knowledge database for assisting in further describing the actual condition of the patient by adding additional data thereto; and
   medical record creating means responsive to said medical term matching means for creating an actual patient medical record, said medical record creating means including draft record generating means for generating a draft medical record related to the at least one medical personnel's dictation for review by the at least one medical personnel, record revising means responsive to the at least one medical personnel for revising the draft medical record, and record accepting means responsive to medical personnel for accepting the draft medical record.

2. An apparatus as defined in claim 1, further comprising medical record storing means responsive to said medical record creating means for storing an accepted medical record created therefrom for future reference.

3. An apparatus as defined in claim 1, wherein said knowledge database includes a structured tree configuration.

4. An apparatus as defined in claim 1, wherein said voice processing means includes speech term learning means for learning speech terms used by identified medical personnel.

5. An apparatus as defined in claim 1, wherein said voice processing means includes speech pattern learning means for learning speech patterns used by identified medical personnel.

6. An apparatus as defined in claim 1, further comprising biometric identifying means connected to said voice processing means for identifying biometric data from medical personnel to thereby reference previous terms or patterns from previous dictations to the apparatus by the identified medical personnel.

7. An apparatus as defined in claim 1, wherein said key term recognizing means further includes non-key term storing means responsive to said non-key term eliminating means for storing the eliminated non-key terms for future reference.

8. An apparatus as defined in claim 1, wherein said record revising means includes knowledge database revised term matching means responsive to said knowledge database for matching terms revised by the at least one medical personnel with terms in said knowledge database.

9. A medical record forming and storing apparatus comprising:
   voice inputting means for inputting unprompted and unstructured free dictation of at least one medical personnel;
   voice processing means responsive to said voice inputting means for processing the inputted voice from said voice inputting means and generating voice data therefrom;
   key term recognizing means responsive to said voice data processing means for recognizing key medical terms freely dictated in an unstructured and unprompted format by the at least one medical personnel, said key term recognizing means including key medical term storing means for storing a plurality of key medical terms, comparing means responsive to said key medical term storing means for comparing the voice data with key medical terms within said key medical term storing means, and separating means responsive to said comparing means for separating the key medical terms from the non-key medical terms;
   medical term matching means responsive to said key term recognizing means for matching medical terms used by the medical personnel at least with patient conditions, said medical term matching means including a knowledge database for assisting in further describing the actual condition of the patient by adding additional data thereto; and
   medical record creating means responsive to said medical term matching means for creating an actual patient medical record, said medical record creating means including draft record generating means for generating a draft medical record related to the at least one medical personnel's dictation for review by the at least one medical personnel, record revising means responsive to the at least one medical personnel for revising the draft medical record, the record revising means including knowledge database revised term matching means responsive to said knowledge database for matching terms revised by the at least one medical personnel with terms in said knowledge database, the knowledge database revised term matching means including best-fit comparing means for comparing the revised term with terms within said knowledge database based upon a best-fit matching configuration, and record accepting means responsive to medical personnel for accepting the draft medical record.

10. An apparatus as defined in claim 1, further comprising a medical personnel user interface responsive to said medical record creating means for providing a user interface to medical personnel so that draft medical records can be revised.

11. A medical recording forming and storing apparatus comprising:
   a voice input device for inputting unprompted and unstructured free dictation of at least one medical personnel;
   a voice processor responsive to said voice input device for processing the inputted voice and generating voice data therefrom;
   a key term recognizer responsive to said voice processor for recognizing key medical terms freely dictated by the at least one medical personnel, said key term recognizer including a key medical term database for storing a plurality of key medical terms therein and a non-key term eliminator for eliminating non-key terms from the generated voice data;
   a medical term matcher responsive to said key word recognizer for matching recognized key medical terms used by the at least one medical personnel at least with patient conditions to thereby add additional data thereto, including a knowledge database having a structured tree configuration which relates patient conditions with patient treatments of the conditions so that the knowledge database assists in further describing the actual condition of the patient by adding additional data thereto;
   a medical record creator responsive to said medical term matcher for creating an actual patient medical record therefrom;
   medical record storing means responsive to said medical record creator for storing an accepted medical record created therefrom for future reference.

12. An apparatus as defined in claim 11, wherein said voice processor includes a speech term learner for learning speech terms used by identified medical personnel.

13. An apparatus as defined in claim 11, wherein said voice processor includes a speech pattern learner for learning speech patterns used by identified medical personnel.

14. An apparatus as defined in claim 11, further comprising a biometric identifier connected to said voice processor for identifying biometric data from medical personnel to thereby reference previous terms or patterns from previous dictations to the apparatus by the identified medical personnel.

15. An apparatus as defined in claim 11, wherein said key term recognizer further includes non-key term storing means responsive to said non-key term eliminator for storing the eliminated non-key terms for future reference.

16. An apparatus as defined in claim 15, wherein said medical record creator includes a draft record generator for generating a draft medical record related to the at least one medical personnel's dictation for review by the at least one medical personnel, a record revisor responsive to the at least one medical personnel for revising the draft medical record, and record acceptor responsive to medical personnel for accepting the draft medical record.

17. An apparatus as defined in claim 16, wherein said record revisor includes a knowledge database revised term matcher responsive to said knowledge database for matching terms revised by the at least one medical personnel with terms in said knowledge database.

18. An apparatus as defined in claim 17, wherein said knowledge database revised term matcher includes a best-fit comparator for comparing the revised term with terms within said knowledge database based upon a best-fit matching configuration.

19. An apparatus as defined in claim 18, further comprising a medical personnel user interface responsive to said medical record creator for providing a user interface to medical personnel so that draft medical records can be revised.

20. A medical record forming apparatus comprising:
   voice inputting means for inputting dictation of at least one medical personnel;
   voice processing means responsive to said voice inputting means for processing the inputted voice from said voice inputting means and generating voice data therefrom;
   key term recognizing means responsive to said voice processing means for recognizing key medical terms dictated the at least one medical personnel, said key term recognizing means including key medical term storing means for storing a plurality of key medical terms, comparing means responsive to said key medical term storing means for comparing the voice data with key medical terms within said key medical term storing means, separating means responsive to said comparing means for separating the key medical terms from the non-key medical terms, and non-key term eliminating means for eliminating non-key terms from the generated voice data;
   medical term matching means responsive to said key term recognizing means for matching medical terms used by the medical personnel at least with patient conditions, said medical term matching means including a knowledge database relating patient conditions with patient treatments of the conditions so that the knowledge database assists in further describing the actual condition of the patient by adding additional data thereto; and
   medical record creating means responsive to said medical term matching means for creating an actual patient medical record, said medical record creating means including draft record generating means for generating a draft medical record related to the at least one medical personnel's dictation for review by the at least one medical personnel, record revising means responsive to the at least one medical personnel for revising the draft medical record, and record accepting means responsive to medical personnel for accepting the draft medical record.

21. An apparatus as defined in claim 20, further comprising medical record storing means responsive to said medical record creating means for storing an accepted medical record created therefrom for future reference.

22. An apparatus as defined in claim 21, wherein said knowledge database includes a structured tree configuration.

23. An apparatus as defined in claim 22, wherein said voice processing means includes speech term learning means for learning speech terms used by identified medical personnel.

24. An apparatus as defined in claim 23, wherein said voice processing means includes speech pattern learning means for learning speech patterns used by identified medical personnel.

25. An apparatus as defined in claim 24, further comprising biometric identifying means connected to said voice processing means for identifying biometric data from medical personnel to thereby reference previous terms or patterns from previous dictations to the apparatus by the identified medical personnel.

26. An apparatus as defined in claim 22, wherein said key term recognizing means further includes non-key term storing means responsive to said non-key term eliminating means for storing the eliminated non-key terms for future reference.

27. An apparatus as defined in claim 22, wherein said record revising means includes knowledge database revised term matching means responsive to said knowledge database for matching terms revised by the at least one medical personnel with terms in said knowledge database.

28. An apparatus as defined in claim 27, wherein said knowledge database revised term matching means includes best-fit comparing means for comparing the revised term with terms within said knowledge database based upon a best-fit matching configuration.

29. An apparatus as defined in claim 28, further comprising a medical personnel user interface responsive to said medical record creating means for providing a user interface to medical personnel so that draft medical records can be revised.

30. A method of forming medical records comprising the steps of:
  inputting unprompted and unstructured free dictation of at least one medical personnel;
  processing the inputted voice to thereby generate voice data therefrom;
  recognizing key medical terms freely dictated by the at least one medical personnel responsive to a key medical term database having a plurality of key medical terms stored therein, including the step of eliminating non-key terms from the generated voice data;
  matching recognized key medical terms used by the at least one medical personnel at least with known patient conditions to thereby add additional data thereto, including providing a knowledge database having a structured tree configuration which relates patient conditions with patient treatments of the conditions so that the knowledge database assists in further describing the actual condition of the patient by adding additional data thereto;
  creating an actual patient medical record therefrom; and
  storing a created actual medical record accepted by the at least one medical personnel for future reference.

31. A method as defined in claim 30, wherein the processing step includes learning speech terms used by identified medical personnel.

32. A method as defined in claim 30, wherein the processing step includes learning speech patterns used by identified medical personnel.

33. A method as defined in claim 30, further comprising identifying biometric data from medical personnel to thereby reference previous terms or patterns from previous dictations by the identified medical personnel.

34. A method as defined in claim 30, wherein the recognizing step further includes storing the eliminated non-key terms for future reference.

35. A method as defined in claim 30, wherein the creating step includes generating a draft medical record related to the at least one medical personnel's dictation for review by the at least one medical personnel, revising the draft medical record responsive to the at least one medical personnel, and accepting the draft medical record.

36. A method as defined in claim 35, wherein the revising step includes providing a knowledge database revised term matcher responsive to the knowledge database for matching terms revised by the at least one medical personnel with terms in the knowledge database.

37. A method as defined in claim 36, wherein the knowledge database revised term matcher includes a best-fit comparator for comparing the revised term with terms within the knowledge database based upon a best-fit matching configuration.

38. A method as defined in claim 37, further comprising providing a user interface to medical personnel so that the draft medical records can be revised.

39. A method of forming medical records comprising the step of:
  inputting dictation of at least one medical personnel;
  processing the inputted voice to thereby generate voice data therefrom;
  recognizing key medical terms dictated by the at least one medical personnel responsive to a key medical term database having a plurality of key medical terms stored therein and eliminating non-key terms from the generated voice data;
  matching recognized key medical terms used by the at least one medical personnel at least with known patient conditions; and
  providing a knowledge database having a structured tree configuration for assisting in further describing the actual condition of the patient by adding additional data thereto.

40. A method as defined in claim 39, further comprising creating an actual patient medical record responsive to the matched recognized key medical terms and storing a created medical record accepted by the at least one medical personnel for future reference.

41. A method as defined in claim 39, wherein the structure tree of said knowledge database includes at least a root node and a plurality of leaf nodes.

42. A method as defined in claim 39, wherein the processing step includes learning speech terms used by identified medical personnel.

43. A method as defined in claim 42, wherein the processing step includes learning speech patterns used by identified medical personnel.

44. A method as defined in claim 43, further comprising identifying biometric data from medical personnel to thereby reference previous terms or patterns from previous dictations by the identified medical personnel.

45. A method as defined in claim 44, wherein the recognizing step further includes storing the eliminated non-key terms for future reference.

46. A method as defined in claim 40, wherein the creating step includes generating a draft medical record related to the at least one medical personnel's dictation for review by the at least one medical personnel, revising the draft medical record responsive to the at least one medical personnel, and accepting the draft medical record.

47. A method as defined in claim 46, wherein the revising step includes providing a knowledge database revised term matcher responsive to the knowledge database for matching terms revised by the at least one medical personnel with terms in the knowledge database.

48. A method as defined in claim 47, wherein the knowledge database revised term matcher includes a best-fit comparator for comparing the revised term with terms within the knowledge database based upon a best-fit matching configuration.

49. A method as defined in claim 48, further comprising providing a user interface to medical personnel so that the draft medical records can be revised.

50. A method of forming medical records comprising the step of:
generating a plurality of key medical terms;
recognizing the plurality of key medical terms responsive to a key medical term database having a plurality of key medical terms stored therein, including eliminating non-key terms from generated data;
matching recognized key medical terms used by the at least one medical personnel at least with known patient conditions stored in a knowledge database which relates patient conditions with patient treatments of the conditions so that the knowledge database assists in further describing the actual condition of the patient by adding additional data thereto; and
creating an actual patient medical record responsive to the matched recognized key medical terms, including generating a draft medical record related to the at least one medical personnel's dictation for review by the at least one medical personnel, revising the draft medical record responsive to the at least one medical personnel, and accepting the draft medical record.

51. A method as defined in claim 50, further comprising storing a created medical record accepted by at least one medical personnel for future reference.

52. A method as defined in claim 50, wherein the recognizing step further includes storing the eliminated non-key terms for future reference.

53. A method as defined in claim 50, wherein the revising step includes providing a knowledge database revised term matcher responsive to the knowledge database for matching terms revised by the at least one medical personnel with terms in the knowledge database.

54. A method as defined in claim 53, wherein the knowledge database revised term matcher includes a best-fit comparator for comparing the revised term with terms within the knowledge database based upon a best-fit matching configuration.

55. A method as defined in claim 54, further comprising providing a user interface to medical personnel so that the draft medical records can be revised.

* * * * *